United States Patent [19]
Farrugia

[11] Patent Number: 5,713,488
[45] Date of Patent: Feb. 3, 1998

[54] CONDOM DISPENSER

[76] Inventor: John V. Farrugia, 11787 Gladstone Ave., Lakeview Terrace, Calif. 91342

[21] Appl. No.: 590,605

[22] Filed: Jan. 24, 1996

[51] Int. Cl.⁶ .................................. A47K 10/24
[52] U.S. Cl. .............................. 221/45; 221/226
[58] Field of Search .................. 221/59, 45, 226, 221/232, 268, 271, 279, 282, 283; 312/35, 42

[56] References Cited

U.S. PATENT DOCUMENTS

| | | | |
|---|---|---|---|
| 1,895,662 | 1/1933 | Horwitt | 221/59 |
| 2,274,866 | 3/1942 | Martens | 221/59 |

*Primary Examiner*—Kenneth Noland

[57] ABSTRACT

A condom dispenser for containing and dispensing individually wrapped condoms. The inventive device includes a dispensing assembly for receiving and dispensing a stack of condoms. A mounting assembly is coupled to the dispensing assembly for releasable mounting the same to a support structure.

5 Claims, 3 Drawing Sheets

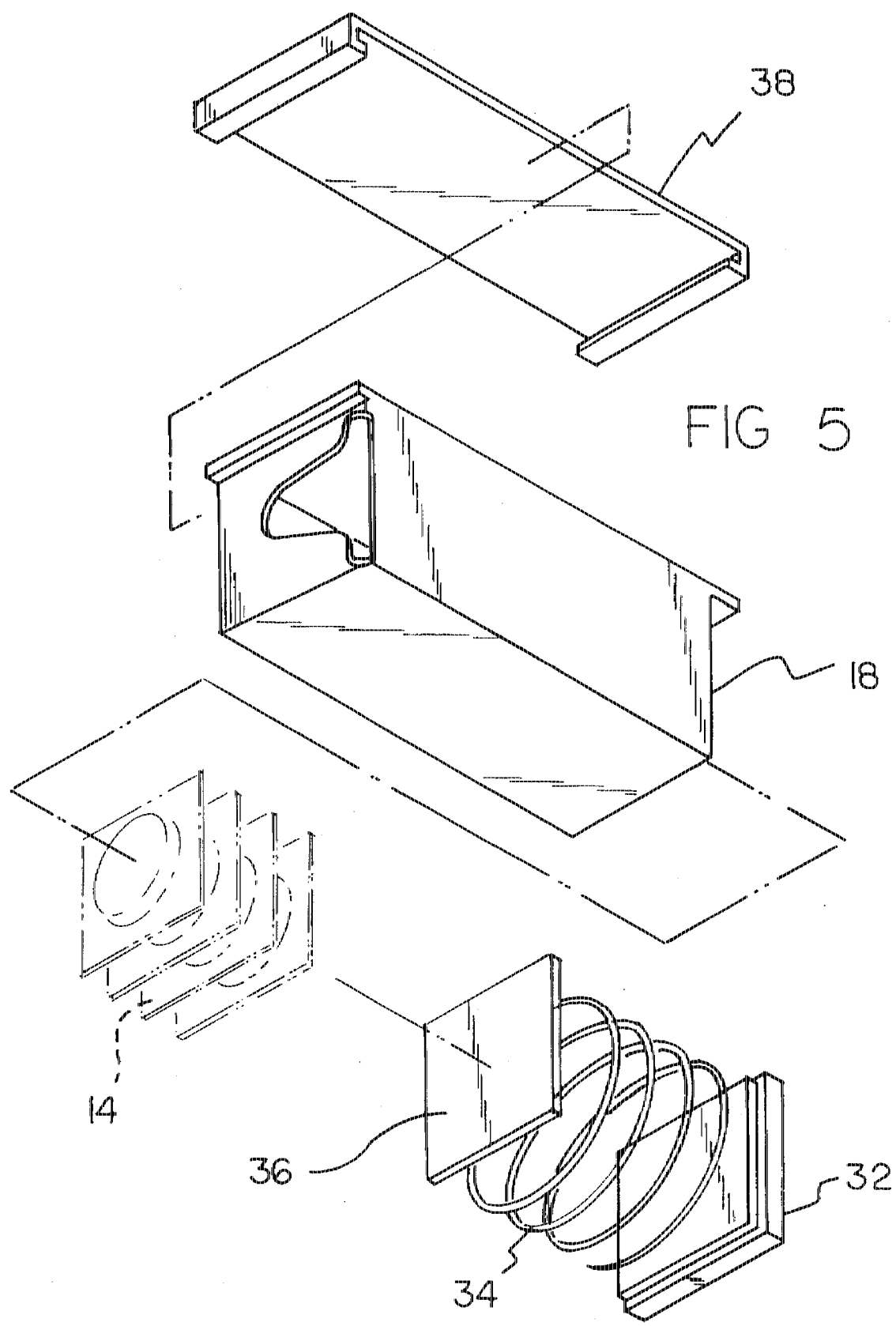

CONDOM DISPENSER

BACKGROUND OF THE INVENTION

1. Field of the Invention

The present invention relates to dispensing devices and more particularly pertains to an condom dispenser for containing and dispensing individually wrapped condoms.

2. Description of the Prior Art

The use of dispensing devices is known in the prior art. More specifically, dispensing devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art dispensing devices include U.S. Pat. Nos. 3,823,845; 4,706,844; 4,858,783; and 5,310,084.

While these devices fulfill their respective, particular objectives and requirements, the aforementioned patents do not disclose a condom dispenser for containing and dispensing individually wrapped condoms which includes a dispensing assembly for receiving a stack of condoms, and a mounting assembly coupled to the dispensing assembly for releasable mounting the same to support structure, wherein the dispensing assembly includes a rectangular container having an access opening through which the condoms can be dispensed.

In these respects, the condom dispenser according to the present invention substantially departs from the conventional concepts and designs of the prior art, and in so doing provides an apparatus primarily developed for the purpose of containing and dispensing individually wrapped condoms.

SUMMARY OF THE INVENTION

In view of the foregoing disadvantages inherent in the known types of dispensing devices now present in the prior art, the present invention provides a new condom dispenser construction wherein the same can be utilized for containing and dispensing individually wrapped condoms. As such, the general purpose of the present invention, which will be described subsequently in greater detail, is to provide a new condom dispenser apparatus and method which has many of the advantages of the dispensing devices mentioned heretofore and many novel features that result in a condom dispenser which is not anticipated, rendered obvious, suggested, or even implied by any of the prior art dispensing devices, either alone or in any combination thereof.

To attain this, the present invention generally comprises a condom dispenser for containing and dispensing individually wrapped condoms. The inventive device includes a dispensing assembly for receiving and dispensing a stack of condoms. A mounting assembly is coupled to the dispensing assembly for releasable mounting the same to a support structure.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new condom dispenser apparatus and method which has many of the advantages of the dispensing devices mentioned heretofore and many novel features that result in a condom dispenser which is not anticipated, rendered obvious, suggested, or even implied by any of the prior art dispensing devices, either alone or in any combination thereof.

It is another object of the present invention to provide a new condom dispenser which may be easily and efficiently manufactured and marketed.

It is a further object of the present invention to provide a new condom dispenser which is of a durable and reliable construction.

An even further object of the present invention is to provide a new condom dispenser which is susceptible of a low cost of manufacture with regard to both materials and labor, and which accordingly is then susceptible of low prices of sale to the consuming public, thereby making such condom dispensers economically available to the buying public.

Still yet another object of the present invention is to provide a new condom dispenser which provides in the apparatuses and methods of the prior art some of the advantages thereof, while simultaneously overcoming some of the disadvantages normally associated therewith.

Still another object of the present invention is to provide a new condom dispenser for containing and dispensing individually wrapped condoms.

Yet another object of the present invention is to provide a new condom dispenser which includes a dispensing assembly for receiving a stack of condoms, and a mounting assembly coupled to the dispensing assembly for releasable mounting the same to support structure.

Even still another object of the present invention is to provide a new condom dispenser wherein the dispensing assembly includes a rectangular container having an access opening through which the condoms can be dispensed.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is an exploded isometric illustration of the invention detailing the components thereof.

DESCRIPTION OF THE PREFERRED EMBODIMENT

Figure 1:
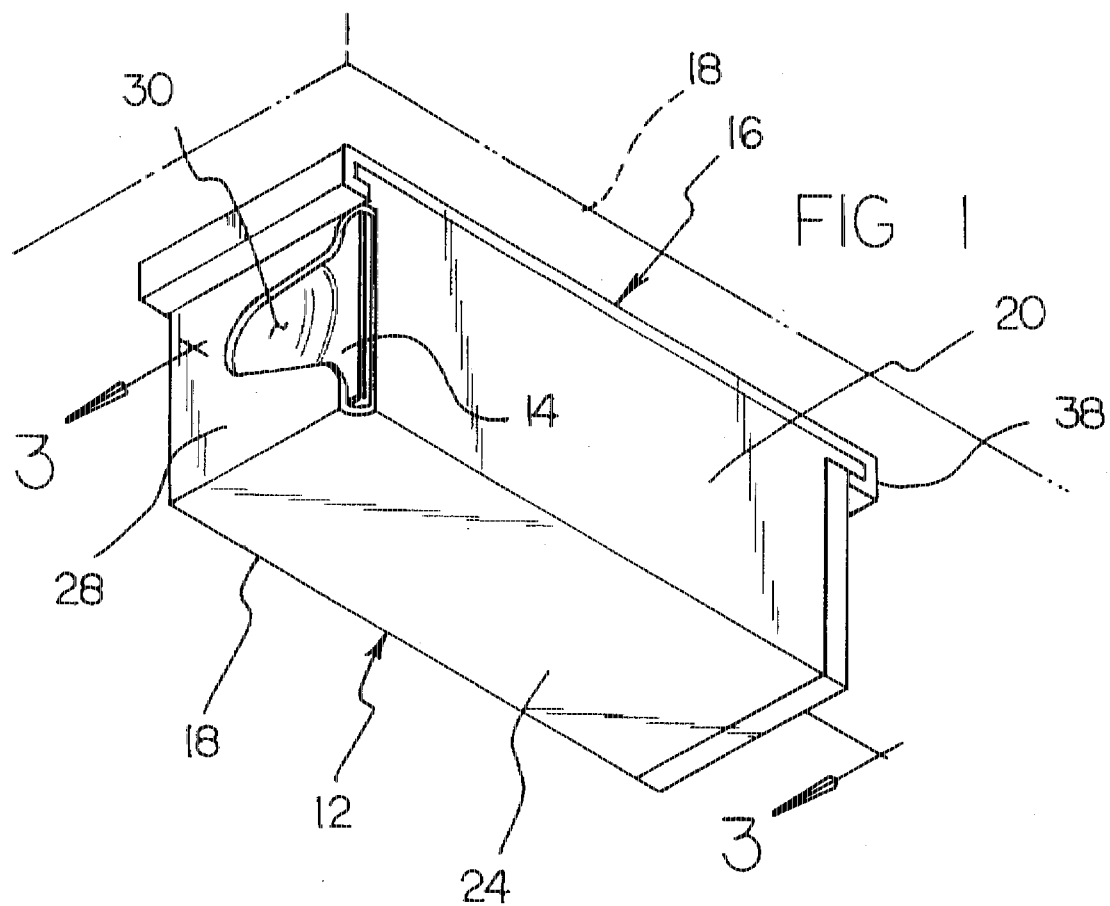
FIG. 1 is an isometric illustration of a condom dispenser according to the present invention as coupled to a support structure.
Figure 2:
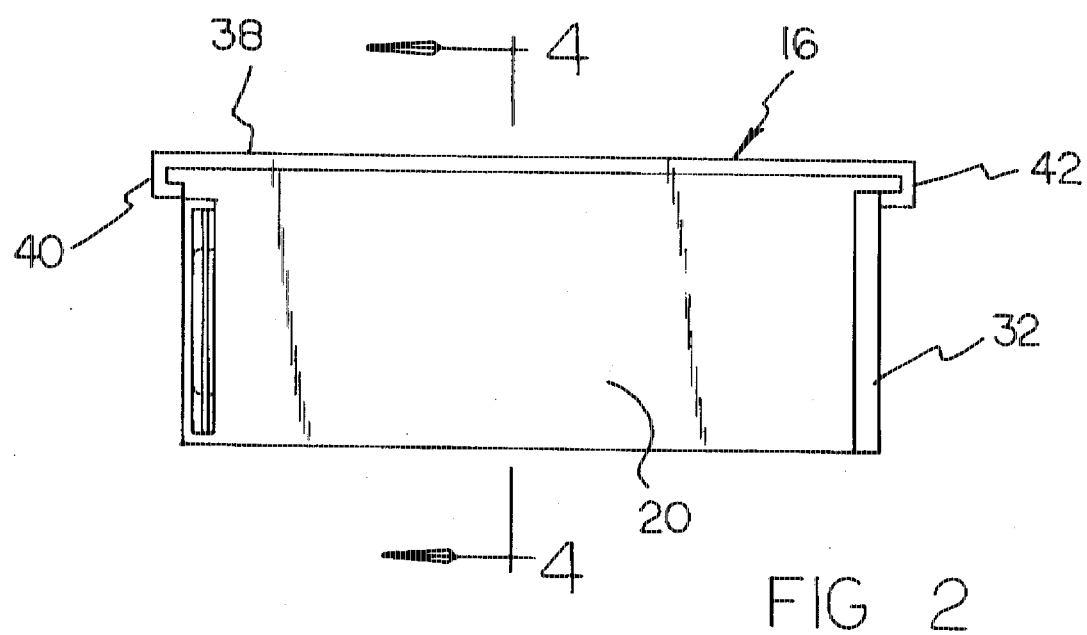
FIG. 2 is a front elevation view of the invention, per

With reference now to the drawings, and in particular to FIGS. 1–5 thereof, a new condom dispenser embodying the principles and concepts of the present invention and generally designated by the reference numeral 10 will be described.

More specifically, it will be noted that the condom dispenser 10 comprises a dispensing means 12 for receiving and dispensing a plurality of condoms 14. A mounting means 16 is releasable coupled to the dispensing means 12 and can be secured to a support surface 18, such as a portion of a bed or like, to support the dispensing means 12 relative thereto. By this structure, condoms 14 can be conveniently stored in an easily accessible position relative to the support structure 18 to which the device 10 is attached.

Figure 3:
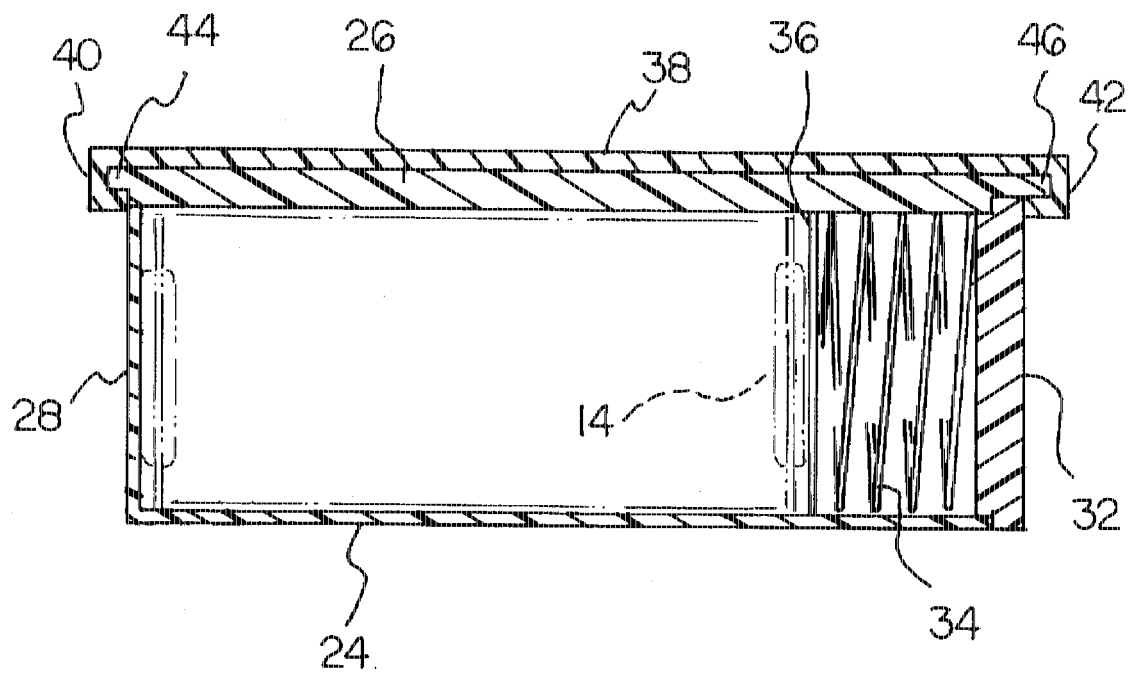
FIG. 3 is a cross sectional view taken along line 3—3 of FIG. 1.
Figure 4:
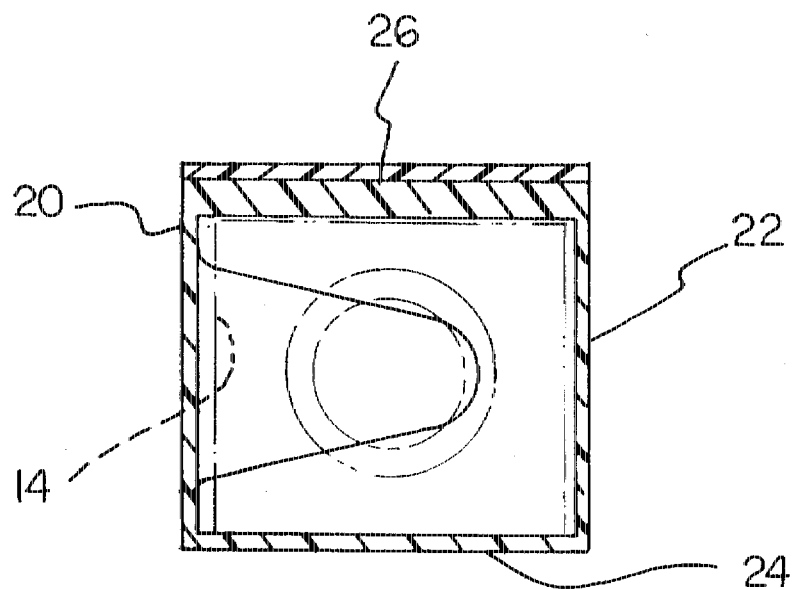
FIG. 4 is a cross sectional view taken along line 4—4 of FIG. 2.

As best illustrated in FIGS. 1 through 5, it can be shown that the dispensing means 12 according to the present invention 10 comprises a rectangular container 18 having a front wall 20 spaced from and oriented substantially parallel to a rear wall 22. A bottom wall 24 and a top wall 26 extends substantially orthogonally between the front and rear walls 20 and 22 so as to define a substantially rectangular cross section of the container as illustrated in FIG. 4. As best illustrated in FIG. 1, a fixed end wall 28 extends substantially orthogonally between the front and rear walls 20 and 22 and the bottom and top walls 24 and 26 to close a first end of the rectangular container 18. An access opening 30 projects through the fixed end wall 28 and continues at least partially onto the front wall 20 to facilitate manual loading of a condom 14 into the interior of the container 18 and the removal of a condom 14 from the interior of the container 18. A end cap 32 which can be either affixed or removably coupled to a second end of the rectangular container 18. As shown in FIG. 3, the end cap 32 is removably coupled to a second end of the rectangular container 18 and preferably secured thereto by a friction or snap fitting engagement. The end cap 32 permits a plurality of condoms 14 to be positioned within the rectangular container such as is illustrated in FIG. 3.

To facilitate biasing of the condoms 14 towards the access opening 30 of the fixed end wall 28, the dispensing means 12 according to the present invention 10 further comprises a coil spring 34 mounted to an interior surface of the end cap 32. The coil spring 34 engages an abutment plate 36 which transfers a force of the spring to the condoms 14 within the container. Thus, as condoms 14 are removed from the dispensing means 12, the remaining condoms will be biased into contact with an interior surface of the fixed end wall 28 for subsequent removal through the access opening 30 thereof.

With continuing reference to FIGS. 1 through 5, it can be shown that the mounting means 16 according to the present invention 10 preferably comprises a mounting bracket 38 removably coupled to the top wall 26 of the rectangular container 18. To this end, the mounting bracket 38 is desirably shaped so as to include a first end channel 40 spaced from and oriented parallel to a second end channel 42. The top wall 26 of the rectangular container 18 is shaped so as to define a first top wall projection 44 which can be slidably positioned within the first end channel 40 of the mounting bracket 38. Similarly, the top wall 26 is further shaped so as to define a second top wall projection 46 which can be slidably positioned within the second end channel 42 of the mounting bracket 38. By this structure, the dispensing means 12 can be slidably engaged to the mounting means 16 to secure the device 10 to a support surface 18 to which the mounting bracket 38 is attached. The mounting bracket 38 can be attached to a support surface 18 through a use of adhesives interposed between the mounting plate and the support surface, or alternatively, through a use of threaded fasteners or other mechanical fasteners directed through the mounting plate and engaged to the support surface. Preferably, the device 10 is mounted beneath or behind a headboard of a bed so as to be concealed from direct view.

In use, the present invention 10 can be easily utilized to removably contain and dispenses a plurality of condoms 14 relative to a support structure 18, such as a bed or the like. The present invention serves to maintain the condoms 14 in an easily accessible position so as encourage use of the condoms to preclude pregnancy and the transfer of sexually transmitted diseases.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A condom dispenser comprising:
   a dispensing means for receiving and dispensing a plurality of condoms; and
   a mounting means releasable coupled to the dispensing means for supporting the dispensing means relative to a support surface;

wherein the dispensing means comprises a rectangular container having a front wall spaced from and oriented substantially parallel to a rear wall, a bottom wall and a top wall extending substantially orthogonally between the front and rear walls so as to define a substantially rectangular cross section of the container, and a fixed end wall extending substantially orthogonally between the front and rear walls and the bottom and top walls to close a first end of the rectangular container, the fixed end wall being shaped so as to define an access opening extending therethrough, and the front wall being shaped so as to define an access opening continuing at least partially onto the front wall, the access openings cooperating to permit manual loading and removal of a condom from an interior of the container; and an end cap affixed to a second end of the rectangular container.

2. The condom dispenser of claim 1, wherein the dispensing means further comprises a coil spring mounted to an interior surface of the end cap; and an abutment plate mounted to a free distal end of the coil spring, the abutment plate being engagable to condoms to bias the same towards the access openings.

3. The condom dispenser of claim 1, wherein the end cap is removably coupled to the second end of the rectangular container.

4. The condom dispenser of claim 1, wherein the mounting means comprises a mounting bracket removably coupled to the top wall of the rectangular container.

5. The condom dispenser of claim 1, wherein the mounting bracket is shaped so as to define a first end channel spaced from and oriented parallel to a second end channel, the top wall of the rectangular container being shaped so as to define a first top wall projection slidably positioned within the first end channel of the mounting bracket and a second top wall projection slidably positioned within the second end channel of the mounting bracket.

* * * * *